United States Patent [19]
Moss et al.

[11] Patent Number: 5,330,460
[45] Date of Patent: Jul. 19, 1994

[54] UNIVERSAL SLITTER HAVING A SLIDER

[75] Inventors: Gordon L. Moss, Bloomington; David A. Liebl, Saint Louis Park, both of Minn.

[73] Assignee: Medamicus, Inc., Minneapolis, Minn.

[21] Appl. No.: 982,591

[22] Filed: Nov. 27, 1992

[51] Int. Cl.$^5$ .......................................... A61M 25/00
[52] U.S. Cl. ................................. 604/280; 604/161; 30/90.4; 30/90.8
[58] Field of Search ............... 604/160, 161, 164, 166, 604/177, 264, 280; 30/90.1, 90.4, 90.8

[56] References Cited

U.S. PATENT DOCUMENTS

| | | | |
|---|---|---|---|
| 3,057,232 | 10/1962 | Cornell, Jr. | 30/90.1 |
| 4,104,791 | 8/1978 | Sunahara | 30/90.1 |
| 4,489,491 | 12/1984 | Gregson | 30/90.7 |
| 4,631,059 | 12/1986 | Wolvek et al. | 604/280 |
| 4,687,469 | 8/1987 | Osypka | 604/161 |
| 4,997,424 | 3/1991 | Little | 604/280 |
| 5,188,606 | 2/1993 | Maloney et al. | 604/161 |

*Primary Examiner*—C. Fred Rosenbaum
*Assistant Examiner*—Corrine Maglione
*Attorney, Agent, or Firm*—Clayton R. Johnson

[57] ABSTRACT

The slitter includes a handle section having a handle member and an arcuate section joined thereto, a knife blade, a clamp member and interfitting parts for mounting the clamp member to the handle members for limited vertical movement between catheter clamping and release positions, each of the arcuate section and the clamp member having vertically opposite facing surfaces for clampingly engaging opposite surface portions of any one of a number of different outer diameter catheters. The arcuate section has a nose portion for entering between the clamped catheter and the introducer when the introducer is to be removed from the catheter without being moved over the proximal terminal end of the catheter. The knife blade is located radially outwardly of the arcuate section surface that abuts against the clamped catheter, extends radially outwardly of the nose and is located rearwardly of the forwardmost part of the nose. In one embodiment the interfitting parts are a protrusion joined to the handle member and a clamp member leg vertical slot of a greater height than the protrusion for having the protrusion extended thereinto for retaining the clamp member and the handle member in face to face abutting relationship.

13 Claims, 3 Drawing Sheets

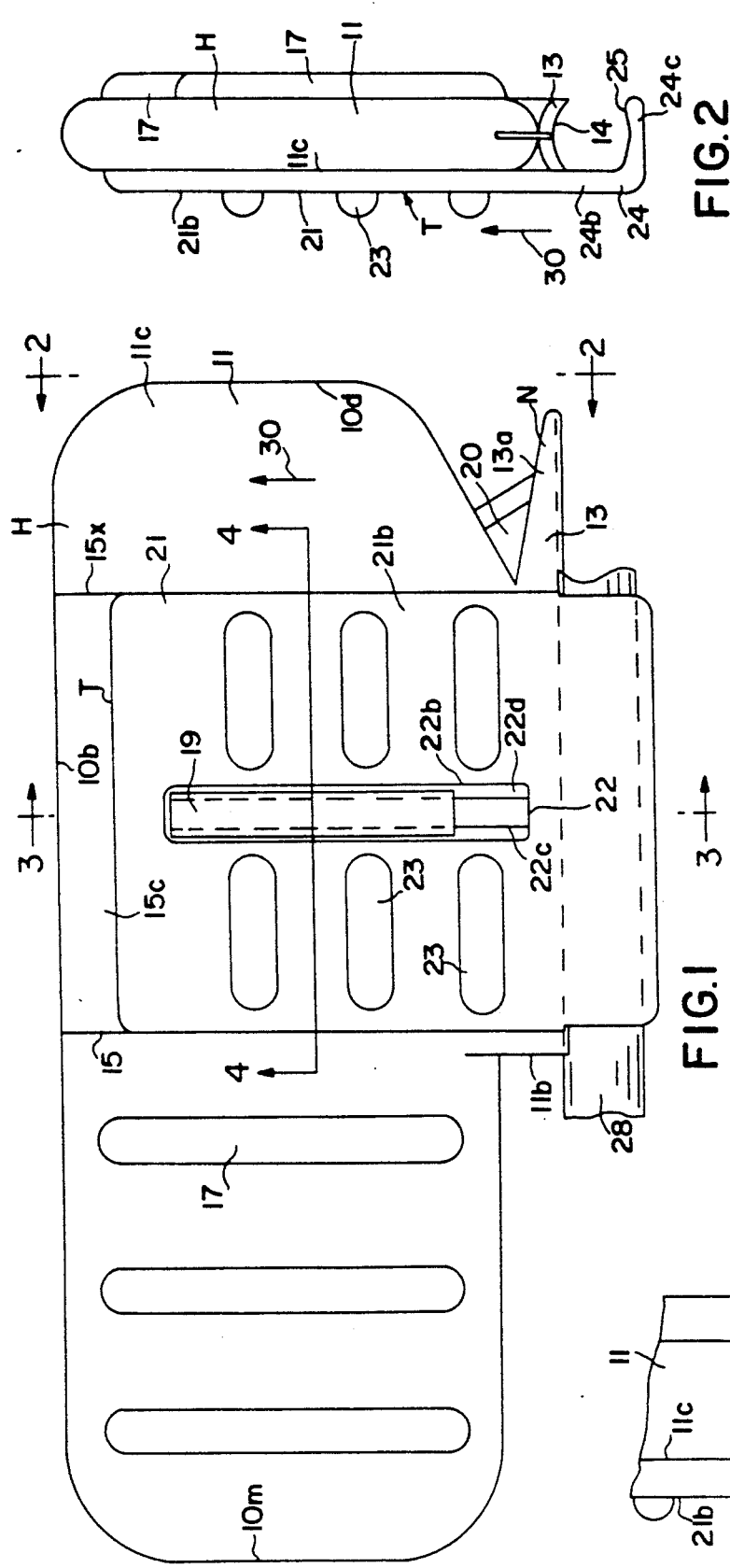
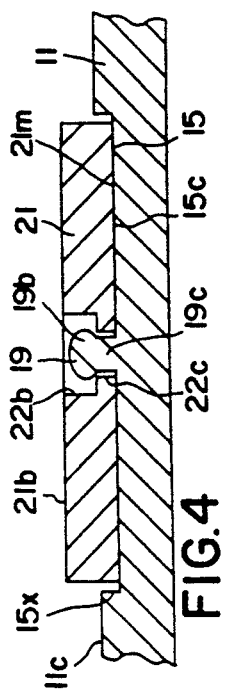
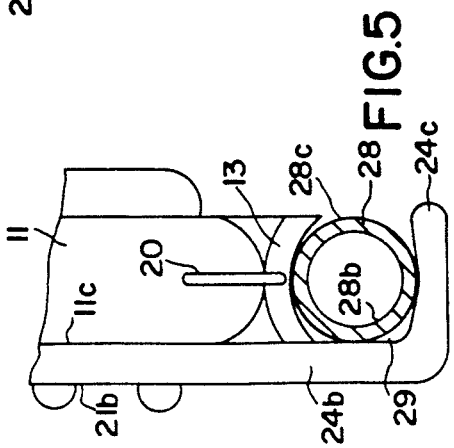

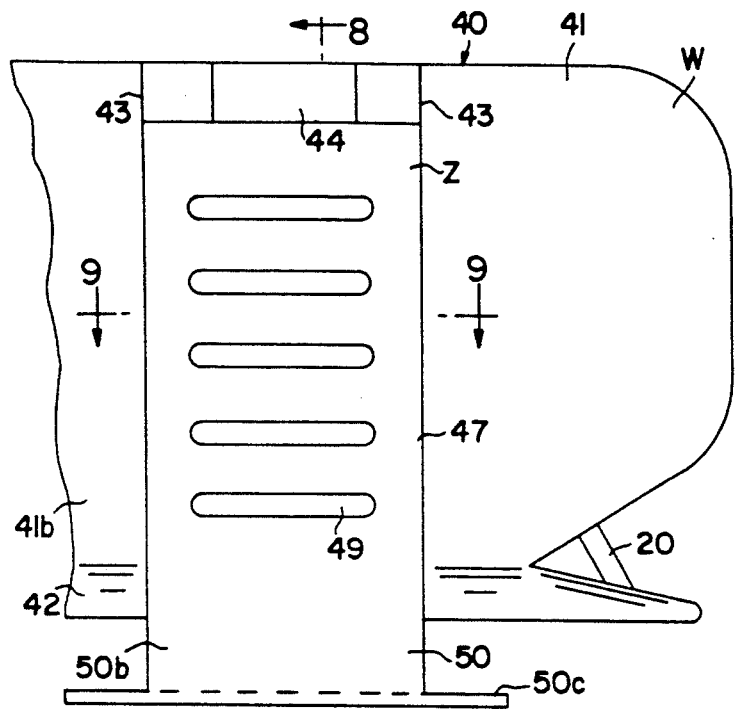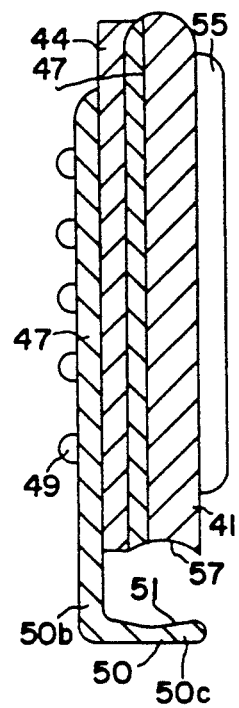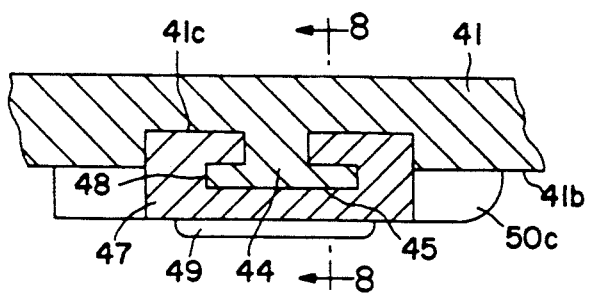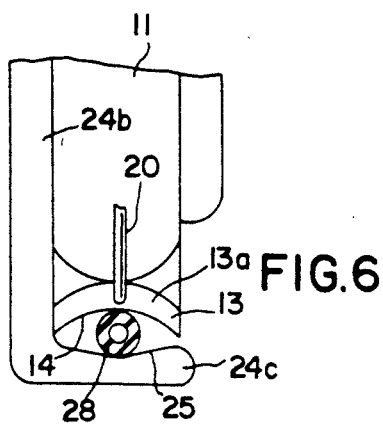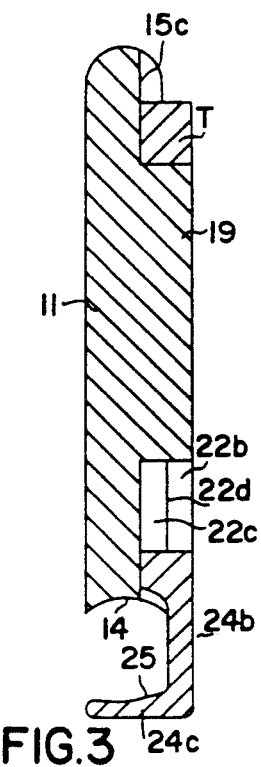

UNIVERSAL SLITTER HAVING A SLIDER

BACKGROUND OF THE INVENTION

This invention relates to the removal of an introducer or cannula from a catheter, pacing lead, or similar item without having to pull the introducer over the proximal end of the catheter, and more particularly to a slitter device that may be used for gripping any one of a multiple number of different outer diameter catheters while the slitter is used for slitting an introducer.

In U.S. Pat. No. 4,997,424 to Little there is disclosed an introducer slitter having an arcuate section extending arcuately through at least 180° to extend partially around a catheter, a handle section joined to the arcuate section to extend away therefrom and a radially extending cutting edge for engaging the introducer tube portion as the introducer is pulled rearwardly relative to the slitter.

In U.S. Pat. No. 3,624,901 to Pettit there is disclosed a wire stripper and cutter that includes a handle which has, at one end, a cutting edge and a hook shaped work support member that is pivoted to the handle adjacent to the cutting edge for supporting a cable as the insulation thereon is slit. In one embodiment the knife is adjustable upwardly and downwardly to avoid having to provide hooks of different sizes for cables of different diameters.

Huff, U.S. Pat. No. 2,141,002, discloses a cable stripper having a substantially semi-cylindrical body section that mounts a knife blade and hinge pins pivotally mounting gates to the body section. Finger and thumb pressure on the gates press them to a closed overlapping position while the palm of the same hand abuts against the body portion. A knife blade extends radially inwardly of an angular plate surface that is abuttable against the radial outer surface of the cable.

In U.S. Pat. No. 4,631,059 to Wovek et al there is disclosed a sheath remover that includes first and second separable body portions to form a bore to have the catheter extend therethrough and squeeze the sheath so that it extends into the path of movement of the cutting edge of the transversely extending knife blade. The two body portions are held together by a plastic hinge.

In U.S. application Ser. No. 07/757,715, filed Sep. 11, 1991, which is assigned to the same assignee as this application, one embodiment of slitter has a handle member that mounts an arcuate portion for abutting against one arcuate section of a catheter and a flexible strap portion hingedly mounted by the handle section to extend around the diametrically opposite arcuate section of the catheter to clamp the catheter against the slitter arcuate section, said slitter having a cutting edge for slitting an introducer. Other embodiments disclosed therein include a handle section having an arcuate portion and a cutting edge and a clamp member hingedly connected to the handle section to cooperate therewith for retaining a catheter in a fixed position relative thereto while an introducer is being pulled to separate the introducer from the catheter.

In order to provide an improved introducer slitter that may be used for slitting introducers for removing the introducers from any one of many different outer diameters catheters without initially having to be slid over the proximal end of the catheter, and which may be easily held while the slitter is being used, this invention has been made.

SUMMARY OF THE INVENTION

The introducer slitter is provided for longitudinally slitting a cannula or an introducer to facilitate the removal of an introducer from a catheter extended therethrough wherein the catheter may be any one of many different outer diameter catheters. The slitter includes a handle section having a handle member or a main body that has an arcuate section joined thereto, the arcuate section including a nose for extending between the introducer and catheter. The slitter also has a clamp section (clamp member) joined to the handle member for slidable movement between an unclamped position and a clamping position for retaining a catheter in clamping engagement with the arcuate section. As a result of the clamp section being slidably mounted, the slitter may be used with catheters with varying outer diameters. Additionally, the slitter may be held by and operated between its unclamped and clamping positions by the thumb and forefinger of one hand of the user. Advantageously there are provided parts forming friction fitting connection between the handle section and clamp member for retaining them in an adjusted condition until the clamp member is manually operated from or toward a catheter clamping position. The slitter has a cutting edge and is at least in part mounted by the handle section main body for slitting the introducer as the introducer is pulled along the catheter toward the slitter.

One of the objects of this invention is to provide new and novel means for clampingly holding a catheter while an introducer is being slit to separate the introducer from the catheter. In furtherance of the above object, it is a further object of this invention to provide an introducer slitter having new and novel means movable between a catheter clamping position and a catheter release position and being usable with catheters of widely varying outer diameters.

BRIEF DESCRIPTION OF THE DRAWINGS

FIG. 1 is a side view of the first embodiment of the slitter of the invention with the clamp section in its maximum unclamping position and having the maximum diameter catheter tubular portion with which the slitter may be used extended between the arcuate section and the clamp jaw;

FIG. 2 is an end view of the first embodiment of the slitter, said view being generally taken along the line and in the direction of the arrows 2—2 of FIG. 1 other than the catheter is no shown;

FIG. 3 is a vertical cross sectional view that is generally taken along the line and in the direction of the arrows 3—3 of FIG. 1, said view not showing the clamp section or handle member ribs;

FIG. 4 is a fragmentary horizontal cross sectional view that is generally taken along the line and in the direction of the arrows 4—4 of FIG. 1, said view not showing the clamp section or handle member ribs;

FIG. 5 is an enlarged fragmentary end view of part of the structure shown in FIG. 1;

FIG. 6 is a view that is the same as that of FIG. 5 other than it shows the clamp section in its minimum outer diameter catheter clamping position and showing a smaller diameter catheter being clamped;

FIG. 7 is a fragmentary side view of the second embodiment of the invention;

FIG. 8 is a vertical cross sectional view of the second embodiment that is generally taken along the line and in the direction of the arrows 8—8 of FIGS. 7 and 9;

FIG. 9 is a fragmentary cross sectional view that is generally taken along the line and in the direction of the arrows 9—9 of FIG. 7;

Figure 10:
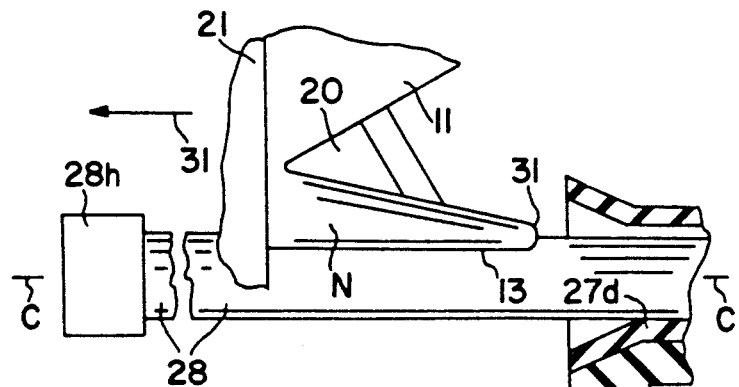
FIG. 10 is an enlarged fragmentary side view of the nose portion of the first embodiment of the slitter and the proximal end portion of an introducer that is shown in cross section in a position for being pulled to be slitted.

Referring in particular to FIGS. 1-6, the first embodiment of the introducer slitter, generally designated 10, includes an axially elongated handle section H. The handle section has a front edge 10d, a rear edge 10m and a top edge 10b, and includes a main body (handle member) 11 that has a lower edge portion integrally joined to the axially elongated arcuate section 13. The front end portion of the arcuate section comprises a nose portion N, the nose section in conjunction with the main body as viewed from the side provides a forwardly opening, generally V-shaped notch. The top surface at the transverse center part of the nose portions extends axially rearwardly in an upwardly inclined direction at an angle of, for example 6°-15°. The maximum thickness and the maximum transverse dimension from the front apex edge 31 each progressively increase in a rearward direction.

The handle member has at least top and rear edge portions of a knife blade 20 embedded therein and at least the lower front corner portion embedded in the nose section. The lower part of the front edge portion of the handle member is inclined to extend downwardly and rearwardly to intersect with the rear part of the nose portion. From the intersection of the handle member front edge 10d with the nose portion, the nose portion extends downwardly and forwardly. The unembedded part of the cutting edge portion of the blade 20 extending forwardly of the axially adjacent parts of the handle member and nose portion. The front part of the nose portion extends axially forwardly of the cutting edge for entering between the introducer inner wall 27d and the catheter tubular portion outer peripheral wall 28c as the introducer is pulled rearwardly relative to the catheter. Accordingly, the non-embedded cutting edge portion of the knife blade is engagable with the introducer 27 which is to be slitted as the introducer is pulled in a proximal direction, the non-embedded cutting edge portion being of a radial dimension that is greater than the radial thickness of the introducer tubular portion 27c of the introducer. The entire knife blade is radially outwardly of the radial inner, arcuately curved surface (inner peripheral wall) 14 of the arcuate section, the cutting edge extending radially outwardly of the nose section in a rearward direction. Thus as may be seen from FIGS. 1 and 6, the unembedded part of the knife blade, including the unembedded (exposed) part of the cutting edge, extends radially outwardly of the outer peripheral surface 13a of the nose section, surface 13a being radially opposite surface 14.

A generally rectangular cut out (slider recess) 15 is provided in the main body axially intermediate portion and is of an axial dimension slightly greater than the corresponding dimension of the slider (clamp section) T. Advantageously the cut out is of a transverse dimension (depth) that is less than the corresponding dimension of the slider. Further, the cut out extends to open through each of the top and bottom edges of the main body and the transversely adjacent part of the arcuate section.

A vertically elongated protrusion 19 is joined to the axial planar, vertical surface 15c of recess 15 and is axially intermediate opposite, transverse vertical edges 15x that in part define the recess. Additionally, the protrusion is vertically spaced from each of the top and bottom edges of the main body and extends further transversely outward of the surfaces 15c than from the side surfaces 11c of the main body. The surfaces 11c are on the same transverse side of the slitter as the protrusion and are axially on either side of the recess. However, the surfaces 11c may be coplanar and parallel to surface 15c. As may be seen in FIG. 4, the protrusion has a vertically elongated neck portion 19c that is joined to the main body at the recess surface 15c to extend transversely outwardly from surface 15c. Further, the protrusion has a vertically elongated, axially enlarged bead 19b transversely spaced from surface 15c and integrally joined to the neck portion. Advantageously, each of the neck portion and the bead extend the vertical dimension of the protrusion. The main body 11 has a plurality of vertically elongated ribs 17 joined thereto, is sufficiently rigid such that it retains its shape during normal use, and provides a gripping advantage when grasped between the thumb and finger.

The slider (clamp section) T, as viewed from the side, is generally rectangular, and has a main portion (vertical leg portion) 21 and an angle jaw 24. The slider also has an axially intermediate, vertically elongated slot 22 that is vertically spaced from each of the top and bottom edges of the main portion. Ribs 23 are joined to the generally planar surface 21b of the slider main portion to extend transversely outwardly thereof. The slot has a generally rectangular slot portion 22b opening through surface 21b and a generally rectangular slot portion 22c opening through the transverse opposite, generally planar surface 21m of the slider main body and to the slot portion 22c. The axial dimension of the slot portion 22b is larger than the corresponding dimension of the slot portion 22c to provide axially spaced, vertically elongated ledges 22d. The maximum transverse dimension of the protrusion 19 is greater than the corresponding dimension of the slot portion 22c but less than that of slot portion 22b. Further, the vertical dimension of the protrusion is substantially less than that of slot 22 while the maximum axial dimension of the bead is greater than that of slot portion 22c. Since the slider and protrusion are made of a somewhat flexible plastic, the protrusion can be pushed through the slot portion 22c whereby the enlarged part (bead) of the protrusion is abuttable against the ledges 22d to retain the slider in a slidable mounted relationship to the main body with their adjacent generally parallel planar surfaces 21m, 15c in a slidable abutting relationship. Thus, the protrusion and clamp section slot portions form interfitting parts for retaining the clamp section in abutting sliding relationship to the handle member 11. Further, the cross-sectional shape of the bead and the surfaces defining the slot 22 are of dimensions to provide a friction fit such that the slider will be retained in the selected vertically adjusted position relative to the main body when the clamp jaw 24c of the angle jaw 24 is vertically beneath the arcuate section. Advantageously the slot is axially centered relative to the main portion, and the protrusion is of a somewhat smaller transverse dimension than the corresponding dimension of the slot.

The clamp jaw is axially elongated and extends at generally right angles to the vertical leg portion 24b of the angle jaw 24. The main portion 21 and the vertical leg portion 24b together form a clamp member vertical leg.

Dependingly integrally joined to the slider main portion is the angle jaw 24 which has its axially elongated, vertical leg portion 24b integrally joined to the lower edge of the main portion and its inturned support leg (clamp jaw) 24c joined to the lower part of the vertical leg portion 24b. The vertical axial surface 29 of the leg portion 24b is substantially coplanar with the surfaces 11c of the main body 11. The transverse dimension of the leg portion 24b substantially less than the corresponding dimension of the slider main portion, for example about one third to one half of the slider main portion, and the corresponding dimension of the slider main body is, for example, about one half of that of the main body 21. The corresponding transverse dimension of support leg 24c is substantially greater than that of the handle section main body, for example about twice.

The top surface 25 of clamp jaw 24c in transverse cross section is of a shallow V-shape, opens upwardly toward the transverse center of the arcuate section 13 and may have its V-shape apex transversely spaced from the plane of the vertical axial surface 21b of the slider main portion 21 by a dimension that is about the same as the corresponding spacing of the transverse center of the arcuate section radial inner surface 14 from the surface 21b. In view of the transverse spacing referred to in the preceding sentence, the clamp jaw may have catheters of varying outer diameters transversely centrally supported thereon.

Since the catheter and introducer advantageously may be the same as those disclosed in U.S. Pat. No. 4,997,424, only fragmentary parts have been shown and said catheter and introducer will not be illustrated and described in detail. As in part shown in FIGS. 5 and 10, the introducer 27 has a tubular portion 27c with inner and outer peripheral walls 27d, 27h and a tab portion 27b at the proximal terminal end of the introducer, while the catheter 28 has inner and outer peripheral walls 28b, 28c and a conventional catheter connector, indicated by the box 28h, at the proximal terminal end of the catheter tubular portion. After the catheter or pacing lead 28 has been extended through the introducer 27 and into the blood vessel with the axially adjacent parts of the catheter connector and the proximal terminal end of the introducer tube portion axially spaced by a dimension greater than the axial dimension from the edge 11b to the front end of the nose of the first embodiment of the slitter and the arcuate section spaced from the clamp jaw by a distance greater than the outer diameter of the tubular portion of the catheter, the slitter is moved radially inwardly toward the catheter to have the catheter located between the surfaces 14 and 25, and the nose portion adjacent to the tab portion 27b of the introducer. Now with the slitter being moved to, for example, have the arcuate section surface 14 abutting against the outer diametric surface of the catheter tubular portion, the slider is moved in the direction of the arrow 30 relative to the handle from the unclamped position of FIG. 2 to move the clamp jaw to clampingly retain the adjacent parts of the catheter between the arcuate section and the clamp jaw (clamped position). In moving the slider to its clamping position, the clamp jaw is moved vertically toward the arcuate section.

The slitter may be retained in the clamped position by having one of the thumb and the forefinger abutting against the slider and the other abutting against the opposite surface of the main body. With the introducer thus being gripped, the introducer tab portion is pulled rearwardly in the direction of the arrow 31 by the other hand such that the rear part of the tubular portion 27c of the introducer is pulled over the nose portion, i.e. the nose portion enters radially between the catheter outer peripheral wall and the introducer tubular portion. Then the proximal terminal edge of the introducer tube portion in being moved rearwardly, abuts against the knife cutting edge to slit the introducer tubular portion and the slitted part of the tubular portion is moved downwardly and rearwardly of the knife edge and the radially adjacent part of the catheter. Since the knife cutting edge portion diverges in a rearward direction and the main body extends transversely outwardly on each transverse side of the knife blade, as the slit parts move past the part of the main body adjacent to the knife blade, the slit edges of the introducer tube portion are transversely spread and thence further spread due to moving downwardly in a rearward direction. Thus the introducer is removed from the catheter without having to be pulled over the connector 28h.

The introducer slitter may also be used for slitting an introducer on an electrode head assembly, for example of the type referred in U.S. Pat. No. 4,214,594. However, an advantage of the present invention is that it may be used for slitting the tubular portions of introducers of many more different outer diameters than the first embodiment disclosed in U.S. Pat. No. 4,214,594.

Referring to FIGS. 7-9, the second embodiment of the invention, generally designated 40, is the same as that of the first embodiment, except for the difference set forth hereinafter. The second embodiment includes a handle section W and a clamp section Z. The handle section includes a handle member or main body 41 and an arcuate section 42 that in turn has a nose portion N. One transverse side portion of the main body has a pair of parallel recesses (cut outs) 43 that extend vertically to open through the main body top and bottom edges and through the generally planar side surface 41b of the main body. The recesses in part define the vertical, generally T-shaped protrusion part 44, that is joined to the main body to extend the vertical dimension of the main body and open through the transversely adjacent part of the arcuate section. The protrusion 44 has the transverse outer surface 45 of its cross bar generally parallel to the surface 41b such as shown in FIG. 9, although it is to be understood that it may be coplanar with surface 41b. The cut outs are in part defined by axial vertical surfaces 41c that are parallel to surface 45 and axial opposite vertical transverse surfaces that are axially spaced by an axial dimension slightly greater than the axial dimension of the slider main body portion 47. The cut outs 43, protrusion and the slot 48 of the slider form interfitting parts for slidably connecting the clamp member to the handle member main body. Ribs 55 may be provided on each transverse side of the main body and joined thereto.

The clamp member (slider) Z includes a generally rectangular block portion or main portion 24 that is vertically elongated and an angle jaw 50. The angle jaw includes a vertical leg 50b joined to the lower edge portion of the main portion 47, the vertical leg being of a substantially smaller transverse dimension than that of the of the main portion as are the corresponding parts of the first embodiment. The angle jaw also includes a support leg (clamp jaw) 50c that is joined to the lower edge of the vertical leg 50b to extend transversely away therefrom and axially forwardly and rearwardly of the vertical leg and main portion. The clamp jaw is axially elongated.

The main portion 47 has a vertical T-shaped slot 48 that extends from the vertical leg to open through the top edge of the clamp member. The protrusion 44 is extendable into the slot 48 for slidably mounting the jaw member to the main body. The clamp jaw 50c has an axially elongated, shallow generally V-shaped surface 51 facing the arcuate section. The apex of the surface 51 is transversely centered relative to the axially elongated surface 57 of the arcuate section which opens toward the clamp jaw surface 51.

It is believed the manner of use of the second embodiment is obvious from the description of the use of the first embodiment, each of the embodiments functioning in the same manner for clampingly holding a catheter while an introducer is being slit.

Figure 11:
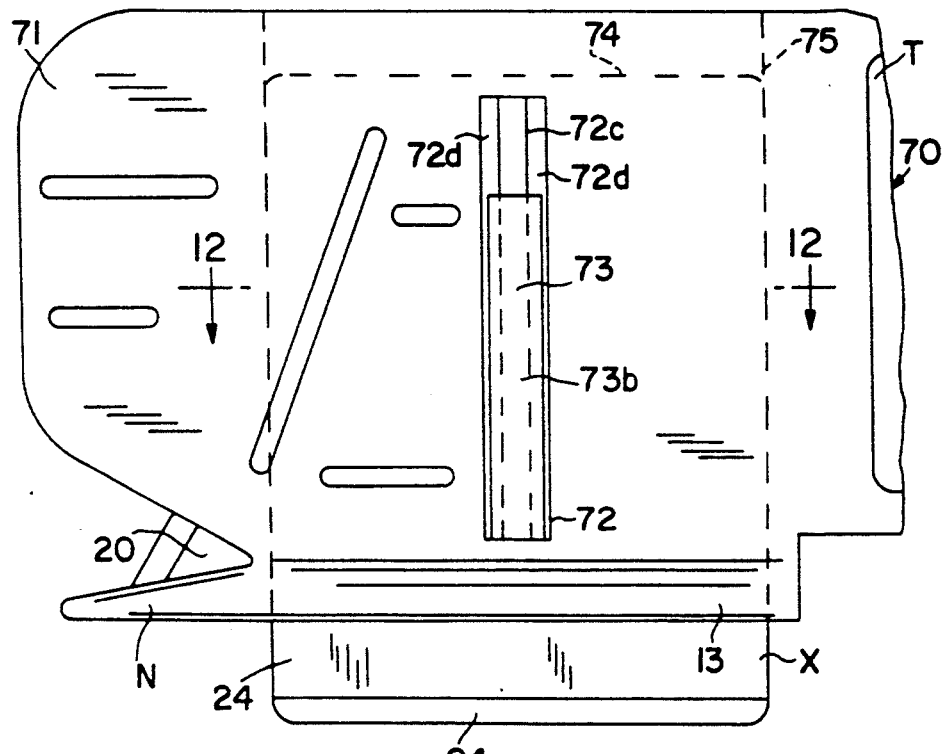
FIG. 11 is a fragmentary side view of the third embodiment of the slitter of the invention with the clamp section in its maximum unclamping position, said view being generally taken along the line and in the direction of the arrows 11 of FIG. 12.
Figure 12:
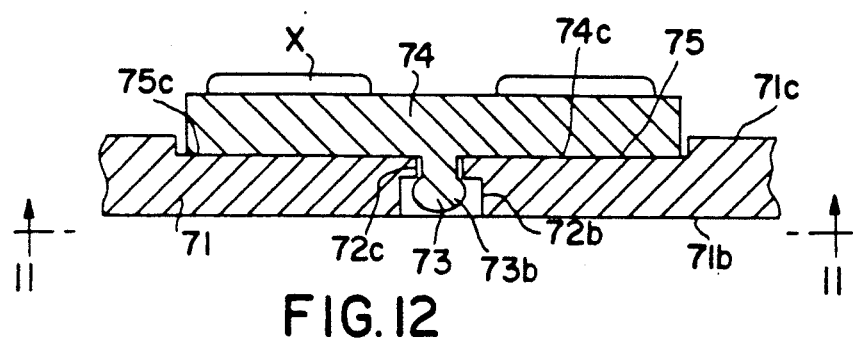
FIG. 12 is a fragmentary cross sectional view that is generally taken along the line and in the direction of the arrows 11—11 of FIG. 12, said view not showing the handle member ribs.

Referring to FIGS. 11 and 12, the third embodiment of the invention, generally designated 70, is the same as the first embodiment, except for the difference set forth hereinafter. The third embodiment includes a handle section T and a clamp section X. The handle section includes a handle member or main body 71 and an arcuate section 13 that in turn has a nose portion N.

The handle member 71 may be the same as handle member 11, except that instead of having a protrusion corresponding to protrusion 19, it has an axially intermediate, vertically elongated slot 72 that is vertically spaced from each of the top and bottom edges of the main body 71. The slot has a generally rectangular slot portion 72b opening through surface 71b of the main body and a generally rectangular slot portion 72c opening through the transverse opposite, generally planar surface 75c of the cut out 75 in the main body and to the slot portion 72b to provide axially spaced, vertically elongated ledges 72d. The cut out opens through the surface 71c which is transversely opposite the surface 71b. Advantageously ribs are joined to the main body 71 to facilitate grasping the handle section.

The clamp section (slider) X may be the same as the clamp section 21 except that instead of having a slot 22 formed therein, it has a vertically elongated protrusion 73 joined to the axial planar, vertical surface 74c of the main portion 74 of the clamp section X and is axially intermediate opposite, transverse vertical edges of the main portion. Additionally, the protrusion is vertically spaced from each of the top and bottom edges of the main portion and extends transversely outwardly of the surfaces 74c. As may be seen in FIG. 12, the protrusion has a vertically elongated neck portion that is joined to the main portion surface 74c to extend transversely outwardly from surface 74c. Further the protrusion has a vertically elongated, axially enlarged bead 73b transversely spaced from surface 74c and integrally joined to the neck portion. The protrusion bead in abutting against ledges 72d retains the surfaces 74c, 75c in slidable abutting relationship to permit the clamp section X being moved relative to the handle section T in the same manner as the corresponding sections of the first embodiment. Since the slotted portion 72 and the protrusion 73 preform the same function and may be of the same shape as the slot 22 and protrusion 19 of the first embodiment other than for being parts of the reverse one of the handle section and clamp section. It is believed the manner of using the third embodiment is apparent from the description of the use of the first embodiment, and accordingly the third embodiment will not be further described.

With reference to each of the embodiments, the cutting edge of the knife blade extends substantially radially relative the central axis of the portion of the catheter that is clampingly engaged by the slitter. Further, the part of the knife that engages the introducer tubular portion to do the slitting extends further forward than any other axially adjacent part of the slitter. Additionally, each arcuate section of the embodiments disclosed herein has a nose portion for extending radially between the clamped catheter and introducer tubular portion and forwardly of the portion of the cutting edge that engages the tubular portion. Additionally, with reference to each embodiment, advantageously the entire clamp member is located axially rearwardly of the entire nose, and is located rearwardly of the cutting edge of the knife blade.

Relative to each of the embodiments, the clamp member in being slidably moved relative to the handle section moves generally perpendicular to the central axis C—C of elongation of the arcuate section. The arcuate section is arcuately curved relative to the central axis to open toward the central axis and may be of a radius of curvature larger than the radius of curvature of the outer diameter of the maximum outer diameter catheter tubular portion that is to be clampingly engaged by the slitter. Also, advantageously, the interfitting parts of each of the embodiments form a friction fit so as to retain the slider and handle section in their relative manually adjusted relationship when no catheter is being clampingly engaged, and to retain the slider in slidable abutting relationship to the handle section.

What is claimed is:

1. An introducer slitter for facilitating the removal of an introducer from a catheter or pacer lead that is of one of a number of different outer diameters and extends through the introducer without sliding the introducer over the proximal end of the catheter wherein the catheter and introducer each has an axially elongated tubular portion with inner and outer peripheral surfaces, comprising a handle section that has a front edge portion and a top edge portion, said handle section having an axially elongated handle member that includes an axially extending lower edge and an axially extending arcuate section joined to the handle member lower edge, said arcuate section being vertically spaced from the top edge and having a radial inner surface for abutting against the catheter outer peripheral surface, means defining a cutting edge joined to the handle section adjacent to the juncture of the handle member to the arcuate section and being radially outwardly of the arcuate section surface, the front edge portion having a front edge part extending radially outwardly relative to the arcuate section and being axially rearwardly of the means defining the cutting edge, a clamp member having clamp means for clampingly abutting against the catheter outer peripheral surface generally diametrically opposite the arcuate section, and retaining means for retaining the clamp member in abutting relationship to the handle section and connecting the clamp member to the handle section for limited slidable movement relative to the handle section between a catheter clamping position that the arcuate section and clamp member cooperatively clampingly engaging the catheter to retain the catheter in an axially fixed clamped position relative to the slitter, and a catheter release position, the clamp means including a clamp jaw for abutting against the catheter and a vertically extending clamp leg having a top axially extending terminal edge and a lower edge joined to the clamp jaw, said clamp jaw being vertically opposite the arcuate section from the top edge in both the clamp member clamping and unclamping positions, the arcuate section having a front nose portion extending axially forwardly of the cutting edge for entering between the introducer inner surface and the catheter outer peripheral surface as the introducer is pulled rearwardly relative to the catheter tubular portion whereby the cutting edge slits the introducer tubular portion as the introducer is pulled rearwardly, the nose portion extending axially forwardly of the clamp jaw, the arcuate section having an outer peripheral surface that defines at least part of the nose portion, the means defining the cutting edge having an exposed part that is adapted to engage the introducer and extends radially outwardly of the arcuate section outer peripheral surface and away from the clamp jaw.

2. The slitter of claim 1 further characterized in that the handle member has axially extending, opposite front and rear edges respectively and a first cut out axially intermediate the front and rear edge portions for having the vertical leg movably extended thereinto to permit manually moving the clamp member relative to the arcuate section to selectively adjust the clamping pressure exerted by the clamp jaw on the catheter as the clamp member is slidably moved relative to the handle section.

3. The slitter of claim 2 further characterized in that the handle member has a second cut out axially intermediate the front and rear edges, the cut outs extending vertically, and parallel to one another and that the leg has a first part extending into the first cut out and a second part extending into the second cut out.

4. The slitter of claim 2 further characterized in that the retaining means comprises a handle member portion defining a vertically elongated slot and a protrusion joined to the clamp member to extend into the slot to vertically slidably retain the clamp member in abutting relationship to the handle member.

5. The slitter of claim 2 further characterized in that the retaining means comprises clamp member means defining a vertically elongated slot and a protrusion joined to the handle member and extended into the slot to vertically slidably retain the clamp member in abutting relationship to the handle member.

6. An introducer slitter for facilitating the removal of an introducer from a catheter or pacer lead that extends through the introducer without having to slide the introducer over the proximal end of the catheter wherein the catheter and introducer each has an axially elongated tubular portion with inner and outer peripheral surfaces, comprising a handle section that has a front edge portion and a rear edge portion, said handle section including an axially elongated handle member that has an axially extending lower edge, and an axially extending arcuate section joined to the handle member lower edge for entering between the introducer inner wall surface and the catheter outer peripheral wall surface, said arcuate section having a radial inner surface for abutting against the catheter outer peripheral surface and a radial outer peripheral surface radially opposite the radial inner surface, means defining a radially extending cutting edge that is joined to the handle section adjacent to the juncture of the handle member to the arcuate section for slitting the introducer tubular portion, the front edge portion having a front edge part extending radially outwardly relative to the arcuate section and being axially rearwardly of the means defining the cutting edge, the cutting edge having an exposed part for slitting introducer tubular portion, the exposed part being radially outwardly of the arcuate section outer peripheral surface and axially forwardly of said front edge part, a clamp member having a first portion for abutting against the catheter outer peripheral surface generally diametrically opposite the arcuate section and a vertically elongated leg having a top terminal edge and a lower edge portion joined to the first portion, and mounting means for retaining the leg in abutting relationship to the handle section and mounting the leg to the handle section for movement between a clamping position that the first portion clamps the catheter against the arcuate section inner surface to retain the catheter in an axially fixed position relative the slitter and a catheter release position.

7. The slitter of claim 6 further characterized in that the mounting means comprises means mounting the leg for translatory movement to permit selectively varying the vertical spacing of the first portion from the arcuate section to accommodate clampingly holding catheters of varying outer diameters.

8. The slitter of claim 6 further characterized in that the leg has a vertically elongated slot and that the mounting means comprises a vertically elongated protrusion of a shorter vertical dimension than the corresponding dimension of the slot, joined to the handle section and extended into the slot to mount the leg for limited vertical movement relative to the handle section.

9. The slitter of claim 6 further characterized in that mounting means comprises a generally T-shaped protrusion that is joined to the handle member to extend vertically and a generally T-shaped slot in the leg for having the protrusion vertically slidably extended thereinto.

10. An introducer slitter for facilitating the removal of an introducer from a catheter or pacer lead that is of one of a number of different outer diameters and extends through the introducer without sliding the introducer over the proximal end of the catheter wherein the catheter and introducer each has an axially elongated tubular portion with inner and outer peripheral wall surfaces, comprising a handle section that has a front edge portion and a top edge portion, said handle section having an axially elongated handle member that includes an axially extending lower edge and an axially extending arcuate section joined to the handle member lower edge, said arcuate section being vertically spaced from the top edge and having a radial inner surface for abutting against the catheter outer peripheral surface, means defining a cutting edge joined to the handle section adjacent to the juncture of the handle member to the arcuate section and being radially outwardly of the arcuate section surface, the front edge portion having a front edge part extending radially outwardly relative to the arcuate section and being axially rearwardly of the means defining the cutting edge, a clamp member having clamp means for clampingly abutting against the catheter outer peripheral surface generally diametrically opposite the arcuate section, the clamp member including a vertically extending clamp leg having a top axially extending terminal edge and a lower edge joined to the clamp jaw and retaining means for retaining the clamp member in abutting relationship to the handle section and connecting the clamp member to the handle section for limited slidable movement relative to the handle section between a catheter clamping position that the arcuate section and clamp member cooperatively clampingly engage the catheter to retain the catheter in an axially fixed clamped position relative to the slitter, and a catheter release position, the clamp means including a clamp jaw for abutting against the catheter, said clamp jaw being vertically opposite the arcuate section from the top edge in both the clamp member clamping and unclamping positions, the handle member having axially extending, opposite front and rear edges respectively and a cut out axially intermediate the front and rear edge portions for having the vertical leg movably extended thereinto to permit manually moving the clamp member relative to the arcuate section to selectively adjust the clamping pressure exerted by the clamp jaw on the catheter as the clamp member is slidably moved relative to the handle section, the retaining means comprising clamp member means defining a vertically elongated slot and a protrusion joined to the handle member and extended into the slot to vertically slidably retain the clamp member in abutting relationship to the handle member, the handle member having parallel, vertical transverse surfaces and an axial vertical surface that define the cut out and the protrusion having a neck portion joined to the handle member at the axial vertical surface and a bead joined to the neck portion transversely remote from the axial vertical surface and being of a greater axial dimension that the corresponding dimension of each of the slot and the neck portion.

11. The slitter of claim 10 further characterized in that the clamp member and protrusion are made of plastic and are of a flexibility to permit the bead being pushed through the slot and of a rigidity to retain the clamp member in abutting relationship to the handle section once the bead is pushed through the slot.

12. An introducer slitter for facilitating the removal of an introducer from a catheter or pacer lead that extends through the introducer without having to slide the introducer over the proximal end of the catheter wherein the catheter and introducer each has an axially elongated tubular portion with inner and outer peripheral wall surfaces, comprising a handle section that has a front edge portion and a rear edge portion and includes an axially elongated handle member having an axially extending lower edge and an axially elongated arcuate section joined to the handle member lower edge, said arcuate section having a radial inner surface for abutting against the catheter outer peripheral surface, means defining a cutting edge joined to the handle section adjacent to the juncture of the handle member to the arcuate section and being radially outwardly of the arcuate section surface, the front edge portion having a front edge part extending radially outwardly relative to the arcuate section and being axially rearwardly of the means defining the cutting edge, a clamp member having a clamp portion to clampingly abut against the catheter outer peripheral surface generally diametrically opposite to the arcuate section and a clamp leg that has a first axial edge and an opposite axial edge joined to the clamp portion for being manually moved to move the clamp portion toward the arcuate section to clampingly retain the catheter in abutting relationship with the arcuate section surface, the handle member having a top edge opposite the lower edge and a generally rectangular cut out axially intermediate the front and rear edge portions that opens through the top and lower edges to have the clamp leg extended thereinto for being manually moved by one of the finger and thumb of one hand of the user while the slitter is being held by one hand of the user to change the clamping pressure exerted on the catheter, and retaining means joined to the handle section for mounting the clamp leg to the handle section and retaining the clamp leg extending within the cut out, the retaining means comprising a handle member portion defining a vertically elongated slot and a protrusion joined to the clamp member to extend into the slot to vertically slidably retain the clamp member in abutting relationship to the handle member, the protrusion having a neck portion joined to the clamp member and a bead joined to the neck portion in transverse spaced relationship to the clamp member, the maximum axial dimension of the bead being greater than the corresponding dimension of the neck portion.

13. An introducer slitter for facilitating the removal of an introducer from a catheter or pacer lead that extends through the introducer without having to slide the introducer over the proximal end of the catheter wherein the catheter and introducer each has an axially elongated tubular portion with inner and outer peripheral wall surfaces, comprising a handle section that has a front edge portion and a rear edge portion and includes an axially elongated handle member having an axially extending lower edge and an axially elongated arcuate section joined to the handle member lower edge, said arcuate section having a radial inner surface for abutting against the catheter outer peripheral surface, means defining a cutting edge joined to the handle section adjacent to the juncture of the handle member to the arcuate section and being radially outwardly of the arcuate section surface, the front edge portion having a front edge part extending radially outwardly relative to the arcuate section and being axially rearwardly of the means defining the cutting edge, a clamp member having a clamp portion to clampingly abut against the catheter outer peripheral surface generally diametrically opposite to the arcuate section and a clamp leg that has a first axial edge and an opposite axial edge joined to the clamp portion for being manually moved to move the clamp portion toward the arcuate section to clampingly retain the catheter in abutting relationship with the arcuate section surface, the handle member having a top edge opposite the lower edge and a generally rectangular cut out axially intermediate the front and rear edge portions that opens through the top and lower edges to have the clamp leg extended thereinto for being manually moved by one of the finger and thumb of one hand of the user while the slitter is being held by one hand of the user to change the clamping pressure exerted on the catheter, and retaining means joined to the handle section for mounting the clamp leg to the handle section and retaining the clamp leg extending within the cut out, the retaining means comprising clamp member means defining a vertically elongated slot and a protrusion joined to the handle member and extended into the slot to vertically slidably retain the clamp member in abutting relationship to the handle member, the protrusion having a neck portion joined to the handle member and a bead joined to the neck portion in transverse spaced relationship to the handle member, the maximum axial dimension of the bead being greater than the corresponding dimension of the neck portion.

* * * * *